US012083106B2

(12) United States Patent
Armendáriz Borunda et al.

(10) Patent No.: US 12,083,106 B2
(45) Date of Patent: *Sep. 10, 2024

(54) METHODS OF USING A PHARMACEUTICAL COMPOSITION CONTAINING PIRFENIDONE IN SUSTAINED-RELEASE TABLET FORM

(71) Applicant: Excalibur Pharmaceuticals, Inc., New York, NY (US)

(72) Inventors: Juan Socorro Armendáriz Borunda, Mexico City (MX); José Agustín Rogelio Magaña Castro, Mexico City (MX); Jorge Cervantes Guadarrama, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 326 days.

This patent is subject to a terminal disclaimer.

(21) Appl. No.: 17/351,151

(22) Filed: Jun. 17, 2021

(65) Prior Publication Data

US 2021/0386724 A1  Dec. 16, 2021

Related U.S. Application Data

(60) Continuation of application No. 16/460,407, filed on Jul. 2, 2019, now Pat. No. 11,040,030, which is a division of application No. 15/831,650, filed on Dec. 5, 2017, now Pat. No. 10,383,862, which is a division of application No. 15/177,760, filed on Jun. 9, 2016, now Pat. No. 9,962,374, which is a division of application No. 14/233,600, filed as application No. PCT/MX2012/000067 on Jul. 13, 2012, now Pat. No. 9,408,836.

(30) Foreign Application Priority Data

Jul. 19, 2011 (MX) .................... MX/a/2011/007675

(51) Int. Cl.
| | |
|---|---|
| *A61K 31/4418* | (2006.01) |
| *A61K 9/00* | (2006.01) |
| *A61K 9/20* | (2006.01) |
| *A61K 31/44* | (2006.01) |
| *A61K 31/4412* | (2006.01) |
| *A61K 31/717* | (2006.01) |
| *A61P 25/02* | (2006.01) |
| *A61P 29/00* | (2006.01) |

(52) U.S. Cl.
CPC ........ *A61K 31/4418* (2013.01); *A61K 9/0053* (2013.01); *A61K 9/2009* (2013.01); *A61K 9/2013* (2013.01); *A61K 9/2054* (2013.01); *A61K 9/2095* (2013.01); *A61K 31/4412* (2013.01); *A61P 25/02* (2018.01); *A61P 29/00* (2018.01); *A61K 31/44* (2013.01); *A61K 31/717* (2013.01)

(58) Field of Classification Search
CPC ....... A61K 31/4418; A61P 25/02; A61P 29/00
See application file for complete search history.

(56) References Cited

U.S. PATENT DOCUMENTS

| | | | |
|---|---|---|---|
| 4,105,782 | A | 8/1978 | Yu et al. |
| 4,256,877 | A | 3/1981 | Karlsson et al. |
| 4,376,118 | A | 3/1983 | Daher et al. |
| 5,009,895 | A | 4/1991 | Lui |
| 5,310,562 | A | 5/1994 | Margolin |
| 5,811,130 | A | 9/1998 | Boettner et al. |
| 5,958,420 | A | 9/1999 | Jenson |
| 6,365,131 | B1 | 4/2002 | Doshi et al. |
| 7,109,246 | B1 | 9/2006 | Hawtin |
| 8,492,412 | B2 | 7/2013 | Castro et al. |
| 8,603,965 | B2 | 12/2013 | Zhou et al. |
| 9,408,836 | B2 | 8/2016 | Borunda et al. |

(Continued)

FOREIGN PATENT DOCUMENTS

| | | |
|---|---|---|
| CA | 2764043 A1 | 12/2010 |
| CN | 1701793 A | 11/2005 |

(Continued)

OTHER PUBLICATIONS

Salazar-Montes et al., "Potent antioxidant role of Pirfenidone in experimental cirrhosis", European Journal of Pharmacology, vol. 595, No. 1-3, pp. 69-77.*
International Preliminary Report on Patentability dated Jan. 28, 2018 for Application No. PCT/MX2017/000129.
International Search Report and Written Opinion dated Apr. 9, 2018 for Application No. PCT/MX2017/000129.
International Search Report and Written Opinion, PCT/MX2018/000071, dated Mar. 28, 2019, 12 pages.
International Preliminary Report on Patentability, PCT/MX2018/000071, dated Jul. 19, 2019, 7 pages.
International Preliminary Report on Patentability dated Aug. 7, 2013 for Application No. PCT/MX2012/000067.

(Continued)

*Primary Examiner* — Kevin E Weddington

(57) ABSTRACT

The instant invention relates to a process for the preparation of a pharmaceutical composition in sustained-release tablet form comprising from 600 milligrams to 2400 milligrams of Pirfenidone (PFD), in such a way that the drug is bioavailable during an extended period of time of 12 hours from its administration. In this way, the anti-fibrotic and anti-inflammatory action of the drug Pirfenidone is optimized. Moreover, the instant invention offers advantages and a higher therapeutic efficacy compared to other pharmaceutical forms of Pirfenidone for oral administration and its therapeutic application in the regression of chronic renal failure secondary to primary glomerulosclerosis; it shows a better activity with regard to the reduction and/or regression of deleterious effects in breast capsular contracture observed after the surgical implantation of breast implants in humans and has an important anti-TNF-α and anti-TGF-β1 action for the treatment of hepatic fibrosis.

20 Claims, 6 Drawing Sheets

(56) References Cited

U.S. PATENT DOCUMENTS

| | | |
|---|---|---|
| 9,949,959 B2 | 4/2018 | Borunda et al. |
| 9,962,374 B2 | 5/2018 | Borunda et al. |
| 10,376,500 B2 | 8/2019 | Castro et al. |
| 10,383,862 B2 | 8/2019 | Borunda et al. |
| 10,792,258 B2 | 10/2020 | Castro et al. |
| 11,013,727 B2 | 5/2021 | Borunda et al. |
| 11,040,030 B2 | 6/2021 | Borunda et al. |
| 11,052,074 B2 | 7/2021 | Borunda et al. |
| 11,083,719 B2 | 8/2021 | Castro et al. |
| 11,576,905 B2 | 2/2023 | Castro et al. |
| 11,766,426 B2 | 9/2023 | Borunda et al. |
| 2003/0103941 A1 | 6/2003 | Crombleholme et al. |
| 2004/0029946 A1 | 2/2004 | Arora et al. |
| 2004/0235946 A1 | 11/2004 | Ott |
| 2005/0059626 A1 | 3/2005 | Van Nest et al. |
| 2005/0267018 A1 | 12/2005 | Blatt et al. |
| 2006/0039931 A1 | 2/2006 | Scheiwe et al. |
| 2006/0051339 A1 | 3/2006 | Sivak |
| 2006/0115503 A1 | 6/2006 | Goyal |
| 2006/0198823 A1 | 9/2006 | Blatt |
| 2007/0054842 A1 | 3/2007 | Blatt et al. |
| 2007/0117841 A1 | 5/2007 | Ozes et al. |
| 2007/0128258 A1 | 6/2007 | Faure et al. |
| 2007/0258946 A1 | 11/2007 | Blatt |
| 2008/0025986 A1 | 1/2008 | Ozes et al. |
| 2008/0319026 A1 | 12/2008 | Gant et al. |
| 2009/0047246 A1 | 2/2009 | Beigelman et al. |
| 2009/0137354 A1 | 5/2009 | Chaudhuri |
| 2010/0221217 A1 | 9/2010 | Porter et al. |
| 2010/0256031 A1 | 10/2010 | Wu et al. |
| 2011/0034495 A1 | 2/2011 | Seiwert et al. |
| 2011/0224265 A1 | 9/2011 | Castro et al. |
| 2012/0283328 A1 | 11/2012 | Modi |
| 2013/0225639 A1 | 8/2013 | Robinson et al. |
| 2013/0245073 A1 | 9/2013 | Castro et al. |
| 2013/0345165 A1 | 12/2013 | Smith et al. |
| 2014/0296300 A1 | 10/2014 | Borunda et al. |
| 2015/0148382 A1 | 5/2015 | Borunda et al. |
| 2015/0231098 A1 | 8/2015 | Castro et al. |
| 2016/0228424 A1 | 8/2016 | Borunda et al. |
| 2016/0287567 A1 | 10/2016 | Borunda et al. |
| 2017/0216268 A1 | 8/2017 | Castro et al. |
| 2018/0066228 A1 | 3/2018 | Smith et al. |
| 2018/0092893 A1 | 4/2018 | Borunda et al. |
| 2018/0214434 A1 | 8/2018 | Borunda et al. |
| 2018/0353448 A1 | 12/2018 | Castro et al. |
| 2019/0030012 A1 | 1/2019 | Surber |
| 2019/0160048 A1 | 5/2019 | Biber et al. |
| 2019/0262325 A1 | 8/2019 | Borunda et al. |
| 2019/0290606 A1 | 9/2019 | Castro et al. |
| 2019/0358213 A1 | 11/2019 | Borunda et al. |
| 2020/0016138 A1 | 1/2020 | Castro et al. |
| 2020/0038386 A1 | 2/2020 | Borunda et al. |
| 2020/0061040 A1 | 2/2020 | Borunda et al. |
| 2020/0253944 A1 | 8/2020 | Castro et al. |
| 2021/0093593 A1 | 4/2021 | Castro et al. |
| 2021/0346360 A1 | 11/2021 | Borunda et al. |
| 2021/0401989 A1 | 12/2021 | Borunda et al. |
| 2022/0016096 A1 | 1/2022 | Castro et al. |
| 2023/0117397 A1 | 4/2023 | Aguilar-Cordova et al. |
| 2023/0165819 A1 | 6/2023 | Castro et al. |
| 2023/0181550 A1 | 6/2023 | Borunda et al. |

FOREIGN PATENT DOCUMENTS

| | | |
|---|---|---|
| CN | 101972225 A | 2/2011 |
| CN | 101972236 A | 2/2011 |
| CN | 102488660 A | 6/2012 |
| CN | 102670600 A | 9/2012 |
| CN | 102670632 A | 9/2012 |
| CN | 103550242 A | 2/2014 |
| EP | 1113798 A1 | 7/2001 |
| EP | 1356816 A1 | 10/2003 |
| EP | 2177220 A1 | 4/2010 |
| EP | 2832354 A1 | 2/2015 |
| EP | 2907506 | 8/2015 |
| JP | 8-510251 A | 10/1996 |
| JP | 2002-506820 A | 3/2002 |
| JP | 2006-503026 A | 1/2006 |
| JP | 2011-506446 A | 3/2011 |
| JP | 2014-505733 A | 3/2014 |
| JP | 2014-522861 A | 9/2014 |
| JP | 2015-513359 A | 5/2015 |
| JP | 2015-526528 A | 9/2015 |
| JP | 2016-515525 A | 5/2016 |
| JP | 2016-517444 A | 6/2016 |
| MX | 2013008151 A | 10/2013 |
| WO | 99/047140 A1 | 9/1999 |
| WO | 2000/16775 A1 | 3/2000 |
| WO | 2004/073713 A1 | 9/2004 |
| WO | 2004/078193 A1 | 9/2004 |
| WO | 2004/078194 A1 | 9/2004 |
| WO | 2004/078207 A1 | 9/2004 |
| WO | 2004/089283 A2 | 10/2004 |
| WO | 2005/000227 | 1/2005 |
| WO | 2005/037214 A2 | 4/2005 |
| WO | 2006/122154 A2 | 11/2006 |
| WO | 2007/038315 A2 | 4/2007 |
| WO | 2008/107873 A1 | 9/2008 |
| WO | 2009/022899 A1 | 2/2009 |
| WO | 2010/054294 A1 | 5/2010 |
| WO | 2013/012307 A1 | 1/2013 |
| WO | 2013/147577 A1 | 10/2013 |
| WO | 2013/181691 A1 | 12/2013 |
| WO | 2014/036487 A1 | 3/2014 |
| WO | 2014/055548 A1 | 4/2014 |
| WO | 2016/185182 A1 | 11/2016 |
| WO | 2017/104725 A1 | 6/2017 |
| WO | 2018/088886 A1 | 5/2018 |
| WO | 2018/189012 A1 | 10/2018 |
| WO | 2019/035705 A2 | 2/2019 |

OTHER PUBLICATIONS

International Search Report and Written Opinion dated Nov. 22, 2012 for Application No. PCT/MX2012/000067.
International Preliminary Report on Patentability dated Dec. 1, 2009 for Application No. PCT/MX2008/000107.
International Search Report dated Dec. 9, 2008 for Application No. PCT/MX2008/000107.
International Search Report and Written Opinion dated Jun. 5, 2013 for Application No. PCT/MX2013/000027.
International Preliminary Report on Patentability dated Dec. 19, 2014 for Application No. PCT/MX2013/000099.
International Search Report and Written Opinion dated Aug. 8, 2014 for Application No. PCT/MX2013/000099.
International Search Report and Written Opinion, for Application No. PCT/MX2019/000093, dated Aug. 4, 2020.
International Preliminary Report on Patentability, for Application No. PCT/MX2019/000093, dated Jan. 12, 2021.
International Search Report and Written Opinion, for Application No. PCT/US2021/027335, dated Jul. 12, 2021.
[No Author Listed] Understanding Acne Treatment. Retrieved from https://1www.Webmd.com/skin-problems-and-treatnnents/acne/understanding-acne-treatnnent#5 on Feb. 4, 2019. 5 pages.
[No Author Listed], Allicinnow, "allicin," retrieved online at: http://www.allicinnow.com/allicin/acne-treatmentl, 2 pages (2010).
Armendariz-Borunda et al., A Controlled Clinical Trial With Pirfenidone in the Treatment of Pathological Skin Scarring Caused by Bums in Pediatric Patients, Annals of Plastic Surgery, vol. 68(1):22-28 (2012).
Database WPI Section Ch, Week 200629 Thomson Scientific, London, GB; Class B03, AN 2006-273778, WU, Use of pirfenidone for treating hepatic injury and necrosis and acute lung injury. Shanghai Genomics) p. 7; (2005).
Database WPI Section Ch, Week 201139 Thomson Scientific, London, GB; Class A96, AN 2011-D92901, Li X: 'Sustained-release tablet comprises pirfenidone, substance capable of releasing active ingredient, and additive, Med Pharm Sci& Technology Co , 1 page (2011).

(56) References Cited

OTHER PUBLICATIONS

Database WPI Section Ch, Week 201427 Thomson Scientific, London, GB; Class A96, AN 2014-F77081, Deng C et al., Pharmaceutical composition used for treating hepatic fibrosis, liver fibrosis, liver cirrhosis, and liver cancer comprises pirfenidone, inosine, and auxiliary materials. Sichuan Guokang Pharm Co Ltd, 1 page (2014).
Garcia et al., Pirfenidone effectively reverses experimental liver fibrosis. J Hepatol. Dec. 2002;37(6):797-805.
Josling, Peter Josling's PowerPoint on AllicinCenter Products and Their Uses. retrieved from the internet at: http://allicincenter.com/reference.php?id=products, 15 pages (2013).
Macias-Barragan et al., Methyl-1-Phenyl-2-(1H)-Pyridone Treatment Improves Markers of Hepatic Function and Fibrosis in Steatosis Included By High Fat/Carbohydrate Diet. J Hepatology, Abstract of the International Liver Congress™ 2014—49th Annual Meeting of the European Association for the Study of the Liver, Abstract P428, 'ol. 60(1)Suppl.1: S210 (2014).
Macias-Barragan et al., Pirfenidone LP activates PPARalpha and LXRalpha and results in decreased expression of proinflammatory cytokines and improvement of NASH features induced by high fat/carbohydrate diet. Hepatology—Special Issue: The 67th Annual Meeting of the American Association for the Study of Liver Diseases: The Liver Meeting 2016, Abstract No. 1541: vol. 64(SI): 767A-768A: 2 pages (2016).
Nakanishi et al., Pirfenidone inhibits the induction of iNOS stimulated by interleukin-1beta at a step of NF-kappaE DNA binding in hepatocytes. J Hepatology, vol. 41(5):730-736 (2004).
Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.
Ozes et al., Preclinical activity of pirfenidone (5-methyl-1phenyl-2 (IH)-pyri done) in cell-based models of nonalcoholic steatohepatitis. Hepatology, Abstract 697, 2003;34(4): 495A.
Park et al., Pirfenidone suppressed the development of glomerulosclerosis in the FGS/Kist mouse. J Korean Med Sci. Aug. 2003;18(4):527-33.
Tiwari et al., Applications of Complementary Polymers in HPMC Hydrophilic Extended Release Matrices. Drug Delivery Technology, Formulating Hydrophilic Matrix Systems, 2009;9(7), 7 pages.
Veras-Castillo et al., Controlled clinical trial with pirfenidone in the treatment of breast capsular contracture:Association ofTGF polymorphisms. Annals Plastic Surgery. 2014;70(1):16-22.
Wang et al., Remdesivir and chloroquine effectively inhibit the recently emerged novel coronavirus (2019-nCoV) in vitro. Cell Res. Mar. 2020;30(3):269-271. doi: 10.1038/s41422-020-0282-0. Epub Feb. 4, 2020. PMID: 32020029; PMCID: PMC7054408.
International Preliminary Report on Patentability dated Oct. 9, 2014 for Application No. PCT/MX2013/000027.
International Preliminary Report on Patentability, dated Oct. 27, 2022 for Application No. PCT/US2021/027335.
[No Author Listed], Application of addition polymers in hydrophilic hydroxypropyl methylcellulose extended release matrix tablets. Colorcon China, Inc. China Academic Journal Electronic Publishing House. 2022. 3 pages.
[No Author Listed], Efficacy of Pirfenidone Plus MODD in diabetic foot ulcers. NCT02632877. Last updated: Dec. 17, 2015. Retrieved May 17, 2022 from <https://clinicaltrials.gov/ct2/show/NCT02632877?term=NCT02632877>. 8 pages.
[No Author Listed], Mexico's coronavirus death toll is likely 60% higher than confirmed numbers. Reuters. Mar. 29, 2021. Accessed from <https://www.nbcnews.com/news/latino/mexicos-coronavirus-death-toll-likely-60-higher-confirmed-numbers-rcna531> on Jan. 10, 2023. 3 pages.
[No Author Listed], Severe Outcomes Among Patients with Coronavirus Disease 2019 (COVID-19)—United States, Feb. 12-Mar. 16, 2020. CDC COVID-19 Response Team. MMWR Morb Mortal Wkly Rep. Mar. 27, 2020;69(12):343-346. doi: 10.15585/mmwr.mm6912e2.
Armendáriz-Borunda et al., A pilot study in patients with established advanced liver fibrosis using pirfenidone. Gut. Nov. 2006;55(11):1663-5. doi: 10.1136/gut.2006.107136.
Azuma et al., Double-blind, placebo-controlled trial of pirfenidone in patients with idiopathic pulmonary fibrosis. Am J Respir Crit Care Med. May 1, 2005;171(9):1040-7. doi: 10.1164/rccm.200404-571OC. Epub Jan. 21, 2005.
Bednarek et al., Skin Antiseptics. In:StatPearls. Jan. 2022. Retrieved from https://www.ncbi.nlm.nih.gov/books/NBK507853 Jun. 9, 2022.
Bhatraju et al., Covid-19 in Critically Ill Patients in the Seattle Region—Case Series. N Engl J Med. May 21, 2020;382(21):2012-2022. doi: 10.1056/NEJMoa2004500. Epub Mar. 30, 2020.
Bruss et al., Pharmacokinetics of orally administered pirfenidone in male and female beagles. J Vet Pharmacol Ther. Oct. 2004;27(5):361-7. doi: 10.1111/j.1365-2885.2004.00612.x.
Cain et al., Inhibition of tumor necrosis factor and subsequent endotoxin shock by pirfenidone. Int J Immunopharmacol. Dec. 1998;20(12):685-95. doi: 10.1016/s0192-0561(98)00042-3.
Chen et al., Early detection of nonalcoholic steatohepatitis in patients with nonalcoholic fatty liver disease by using MR elastography. Radiology. Jun. 2011;259(3):749-56. doi: 10.1148/radiol.11101942. Epub Apr. 1, 2011.
Choudhuri et al., SARS-CoV-2 PCR cycle threshold at hospital admission associated with patient mortality. PLoS One. Dec. 31, 2020;15(12):e0244777. doi: 10.1371/journal.pone.0244777.
Didiasova et al., Pirfenidone exerts antifibrotic effects through inhibition of GLI transcription factors. FASEB J. May 2017;31(5):1916-1928. doi: 10.1096/fj.201600892RR. Epub Feb. 1, 2017.
Gancedo et al., Pirfenidone prevents capsular contracture after mammary implantation. Aesthetic Plast Surg. Jan. 2008;32(1):32-40. doi: 10.1007/s00266-007-9051-4.
Gao et al., Pirfenidone Alleviates Choroidal Neovascular Fibrosis through TGF-β/Smad Signaling Pathway. J Ophthalmol. Feb. 10, 2021;2021:8846708. doi: 10.1155/2021/8846708.
Gennaro, Remington's Pharmaceutical Sciences. 1990; 18th Ed. Pages 1288-1289, 1291-1292.
Gu et al., Pirfenidone inhibits cryoablation induced local macrophage infiltration along with its associated TGFb1 expression and serum cytokine level in a mouse model. Cryobiology. Jun. 2018;82:106-111. doi: 10.1016/j.cryobiol.2018.03.012. Epub Apr. 3, 2018.
Guo et al., Pirfenidone inhibits epithelial-mesenchymal transition and pulmonary fibrosis in the rat silicosis model. Toxicol Lett. Jan. 2019;300:59-66. doi: 10.1016/j.toxlet.2018.10.019. Epub Oct. 28, 2018.
Güvenç et al., Pirfenidone Attenue Epidural Fibrosis In Rats By Suppressing TNF-α, IL-1, and α-SMA. J Turk Spin Surg. Jul. 2018;29(3):133-40.
Huang et al., Clinical features of patients infected with 2019 novel coronavirus in Wuhan, China. Lancet. Feb. 15, 2020;395(10223):497-506. doi: 10.1016/S0140-6736(20)30183-5. Epub Jan. 24, 2020. Erratum in: Lancet. Jan. 30, 2020.
Ishinaga et al., TGF-β induces p65 acetylation to enhance bacteria-induced NF-κB activation. EMBO J. Feb. 21, 2007;26(4):1150-62. doi: 10.1038/sj.emboj.7601546. Epub Feb. 1, 2007.
Janka-Zires et al., Topical Administration of Pirfenidone Increases Healing of Chronic Diabetic Foot Ulcers: A Randomized Crossover Study. J Diabetes Res. 2016;2016:7340641. doi: 10.1155/2016/7340641. Epub Jul. 10, 2016.
King et al., A phase 3 trial of pirfenidone in patients with idiopathic pulmonary fibrosis. N Engl J Med. May 29, 2014;370(22):2083-92. doi: 10.1056/NEJMoa1402582. Epub May 18, 2014. Erratum in: N Engl J Med. Sep. 18, 2014;371(12):1172.
Loomba et al., GS-0976 Reduces Hepatic Steatosis and Fibrosis Markers in Patients With Nonalcoholic Fatty Liver Disease. Gastroenterology. Nov. 2018;155(5):1463-1473.e6. doi: 10.1053/j.gastro.2018.07.027. Epub Jul. 27, 2018.
Lopez-De La Mora et al., Role and New Insights of Pirfenidone in Fibrotic Diseases. Int J Med Sci. Oct. 14, 2015;12(11):840-7. doi: 10.7150/ijms.11579.
Mccommis et al., Treating Hepatic Steatosis and Fibrosis by Modulating Mitochondrial Pyruvate Metabolism. Cell Mol Gastroenterol Hepatol. 2019;7(2):275-284. doi: 10.1016/j.jcmgh.2018.09.017. Epub Oct. 10, 2018.

(56) References Cited

OTHER PUBLICATIONS

Moises et al., A Double-blind, Multicenter Study Comparing Pirfenidone and Prednisone for Moderate-to-Severe Pulmonary Fibrosi. Chest J. Jan. 1, 2003;124(4)Suppl:116S. Abstract Only. doi: 10.1378/chest.124.4_MeetingAbstracts.116S-b.

Nagai et al., Open-label compassionate use one year-treatment with pirfenidone to patients with chronic pulmonary fibrosis. Intern Med. Dec. 2002;41(12):1118-23. doi: 10.2169/internalmedicine.41.1118.

Nakazato et al., A novel anti-fibrotic agent pirfenidone suppresses tumor necrosis factor-alpha at the translational level. Eur J Pharmacol. Jun. 20, 2002;446(1-3):177-85. doi: 10.1016/s0014-2999(02)01758-2.

Oku et al., Pirfenidone suppresses tumor necrosis factor-alpha, enhances interleukin-10 and protects mice from endotoxic shock. Eur J Pharmacol. Jun. 20, 2002;446(1-3):167-76. doi: 10.1016/s0014-2999(02)01757-0.

Olivas-Martinez et al., In-hospital mortality from severe COVID-19 in a tertiary care center in Mexico City; causes of death, risk factors and the impact of hospital saturation. PLoS One. Feb. 3, 2021;16(2):e0245772. doi: 10.1371/journal.pone.0245772. Erratum in: PLoS One. May 23, 2022;17(5):e0269053.

Orozco et al., Economic evaluation of topical administration of gel with pirfenidone (KITOSCELL Q®) as an adjuvant in the treatment of patients with diabetic foot ulcers. PMD63. Value in Health. May 2017; 20(5):A246.

Pepin, K., Liver Fat Does Not Affect Liver Stiffness Measured with MR Elastography. Resoundant Fact Sheet. 2019. Accessed from < https://www.resoundant.com/single-post/2019/05/21/fact-sheet-liver-fat-does-not-affect-liver-stiffness-measured-with-mr-elastography> on 2022 Sep. 21. 2 pages.

Raghu et al., Treatment of idiopathic pulmonary fibrosis with a new antifibrotic agent, pirfenidone: results of a prospective, open-label Phase II study. Am J Respir Crit Care Med. Apr. 1999;159(4 Pt 1):1061-9. doi: 10.1164/ajrccm.159.4.9805017.

Rao et al., A Systematic Review of the Clinical Utility of Cycle Threshold Values in the Context of COVID-19. Infect Dis Ther. Sep. 2020;9(3):573-586. doi: 10.1007/s40121-020-00324-3. Epub Jul. 28, 2020. Erratum in: Infect Dis Ther. Aug. 18, 2020.

Ravishankar et al., A brief review on Pleiotropic effects of Pirfenidone—novel and ongoing outcomes. Int J Res Dev Pharm Life Sci. Jan.-Feb. 2019;8(1):6-14. doi: 10.21276/IJRDPL.2278-0238.2019.8(1).6-14.

Rubino et al., Effect of food and antacids on the pharmacokinetics of pirfenidone in older healthy adults. Pulm Pharmacol Ther. Aug. 2009;22(4):279-85. doi: 10.1016/j.pupt.2009.03.003. Epub Mar. 27, 2009.

Ruwanpura et al., Pirfenidone: Molecular Mechanisms and Potential Clinical Applications in Lung Disease. Am J Respir Cell Mol Biol. Apr. 2020;62(4):413-422. doi: 10.1165/rcmb.2019-0328TR.

Schaefer et al., Antifibrotic activities of pirfenidone in animal models. Eur Respir Rev. Jun. 2011;20(120):85-97. doi: 10.1183/09059180.00001111.

Selman et al., Idiopathic pulmonary fibrosis: prevailing and evolving hypotheses about its pathogenesis and implications for therapy. Ann Intern Med. Jan. 16, 2001;134(2):136-51. doi: 10.7326/0003-4819-134-2-200101160-00015.

Selvaraj et al., Diagnostic accuracy of elastography and magnetic resonance imaging in patients with NAFLD: A systematic review and meta-analysis. J Hepatol. Oct. 2021;75(4):770-785. doi: 10.1016/j.jhep.2021.04.044. Epub May 13, 2021.

Suga et al., Preventive effect of pirfenidone against experimental sclerosing peritonitis in rats. Exp Toxicol Pathol. Sep. 1995;47(4):287-91. doi: 10.1016/s0940-2993(11)80261-7.

Sun et al., Pharmacokinetic and pharmacometabolomic study of pirfenidone in normal mouse tissues using high mass resolution MALDI-FTICR-mass spectrometry imaging. Histochem Cell Biol. Feb. 2016;145(2):201-11. doi: 10.1007/s00418-015-1382-7. Epub Dec. 8, 2015.

Sun et al., Pharmacometabolic response to pirfenidone in pulmonary fibrosis detected by MALDI-FTICR-MSI. Eur Respir J. Sep. 15, 2018;52(3):1702314. doi: 10.1183/13993003.02314-2017.

Wang et al., Clinical Features of 69 Cases With Coronavirus Disease 2019 in Wuhan, China. Clin Infect Dis. Jul. 28, 2020;71(15):769-777. doi: 10.1093/cid/ciaa272.

Wilson et al., Another Weapon in the Battle against Idiopathic Pulmonary Fibrosis? Am J Respir Cell Mol Biol. Apr. 2019;60(4):386-387. doi: 10.1165/rcmb.2018-0387ED.

Wu et al., Risk Factors Associated With Acute Respiratory Distress Syndrome and Death in Patients With Coronavirus Disease 2019 Pneumonia in Wuhan, China. JAMA Intern Med. Jul. 1, 2020;180(7):934-943. doi: 10.1001/jamainternmed.2020.0994. Erratum in: JAMA Intern Med. Jul. 1, 2020;180(7):1031.

Wygrecka et al., Pirfenidone exerts anti-fibrotic effects through Inhibition of GLI transcription factors. Pneumologie. Feb. 21, 2018;72(S 01):S114-5. doi: 10.1055/s-0037-1619431.

Zhang et al., Liver fibrosis imaging: A clinical review of ultrasound and magnetic resonance elastography. J Magn Reson Imaging. Jan. 2020;51(1):25-42. doi: 10.1002/jmri.26716. Epub Mar. 12, 2019. Author Manuscript, 32 pages.

Zhang et al., Pirfenidone reduces fibronectin synthesis by cultured human retinal pigment epithelial cells. Aust N Z J Ophthalmol. May 1998;26 Suppl 1:S74-6. doi: 10.1111/j.1442-9071.1998.tb01380.x.

Zhou et al., Clinical course and risk factors for mortality of adult inpatients with COVID-19 in Wuhan, China: a retrospective cohort study. Lancet. Mar. 28, 2020;395(10229):1054-1062. doi: 10.1016/S0140-6736(20)30566-3. Epub Mar. 11, 2020. Erratum in: Lancet. Mar. 28, 2020;395(10229): 1038. Erratum in: Lancet. Mar. 28, 2020;395(10229):1038.

Ziol et al., Noninvasive assessment of liver fibrosis by measurement of stiffness in patients with chronic hepatitis C. Hepatology. Jan. 2005;41(1):48-54. doi: 10.1002/hep.20506.

U.S. Appl. No. 14/233,600, filed May 20, 2014, Armendáriz Borunda et al.

U.S. Appl. No. 15/177,760, filed Jun. 9, 2016, Armendáriz Borunda et al.

U.S. Appl. No. 15/831,650, filed Dec. 5, 2017, Armendáriz Borunda et al.

U.S. Appl. No. 16/544,643, filed Aug. 19, 2019, Armendáriz Borunda et al.

U.S. Appl. No. 16/460,407, filed Jul. 2, 2019, Armendáriz Borunda et al.

U.S. Appl. No. 12/673,304, filed Apr. 28, 2010, Magaña Castro et al.

U.S. Appl. No. 13/893,626, filed May 14, 2013, Magaña Castro et al.

U.S. Appl. No. 15/435,494, filed Feb. 17, 2017, Magaña Castro et al.

U.S. Appl. No. 16/450,150, filed Jun. 24, 2019, Magaña Castro et al.

U.S. Appl. No. 18/458,390, filed Aug. 30, 2023, Magaña Castro et al.

U.S. Appl. No. 16/348,189, filed May 8, 2019, Armendáriz Borunda et al.

U.S. Appl. No. 18/051,937, filed Nov. 2, 2022, Armendáriz Borunda et al.

U.S. Appl. No. 14/388,447, filed Feb. 5, 2015, Armendáriz Borunda et al.

U.S. Appl. No. 15/098,970, filed Apr. 14, 2016, Armendáriz Borunda et al.

U.S. Appl. No. 15/920,822, filed Mar. 14, 2018, Armendáriz Borunda et al.

U.S. Appl. No. 16/534,980, filed Aug. 7, 2019, Armendáriz Borunda et al.

U.S. Appl. No. 18/449,747, filed Aug. 15, 2023, Armendáriz Borunda et al.

U.S. Appl. No. 14/421,616, filed Feb. 13, 2015, Magaña Castro et al.

U.S. Appl. No. 16/008,210, filed Jun. 14, 2018, Magaña Castro et al.

U.S. Appl. No. 16/371,670, filed Apr. 1, 2019, Magaña Castro et al.

U.S. Appl. No. 17/063,458, filed Oct. 5, 2020, Magaña Castro et al.

(56) References Cited

OTHER PUBLICATIONS

U.S. Appl. No. 17/063,459, filed Jun. 30, 2022, Magaña Castro et al.
U.S. Appl. No. 17/063,460, filed Feb. 12, 2020, Magaña Castro et al.
U.S. Appl. No. 17/063,461, filed Oct. 13, 2022, Aguilar-Cordova et al.
PCT/MX2013/000027, Oct. 9, 2014, International Preliminary Report on Patentability.
PCT/US2021/027335, Oct. 27, 2022, International Preliminary Report on Patentability.

* cited by examiner

METHODS OF USING A PHARMACEUTICAL COMPOSITION CONTAINING PIRFENIDONE IN SUSTAINED-RELEASE TABLET FORM

RELATED APPLICATIONS

This application is a continuation of and claims priority under 35 U.S.C. § 120 to U.S. patent application U.S. Ser. No. 16/460,407, filed Jul. 2, 2019, which is a divisional of and claims priority under 35 U.S.C. § 120 to U.S. patent application U.S. Ser. No. 15/831,650, filed on Dec. 5, 2017, which is a divisional of and claims priority under 35 U.S.C. § 120 to U.S. patent application U.S. Ser. No. 15/177,760, filed Jun. 9, 2016 (now U.S. Pat. No. 9,962,374), which is a divisional of and claims priority under 35 U.S.C. § 120 to U.S. patent application U.S. Ser. No. 14/233,600, filed May 20, 2014 (now U.S. Pat. No. 9,408,836), which is a national stage filing under 35 U.S.C. § 371 of International PCT Application, PCT/MX2012/000067, filed Jul. 13, 2012, which claims priority to Mexican Application No. MX/a/2011/007675, filed Jul. 19, 2011, each of which is incorporated herein by reference in their entirety.

FIELD OF THE INVENTION

The present invention relates to a process for the preparation of a pharmaceutical composition containing pirfenidone (PFD) in sustained-release tablet form, offering advantages and a better therapeutic efficacy compared to other oral pharmaceutical forms of pirfenidone and its therapeutic application in the regression of human chronic renal failure, breast capsular contracture and hepatic fibrosis.

BACKGROUND OF THE INVENTION

Pirfenidone is a drug constituted by a small molecule, the chemical name of which is 5-methyl-1-phenyl-2-(1H)-pyridone. It is a non-peptidic synthetic molecule with a molecular weight of 185.23 Dalton. Its chemical formula is $C_{12}H_{11}NO$, and its structure is known. Currently, pirfenidone is under clinical evaluation as a wide spectrum anti-fibrotic drug. Pirfenidone has anti-fibrotic and anti-inflammatory properties that are reflected in its activity of lowering the expression of TGF-β1, TNF-α, PDGF and most importantly, the expression of different types of collagens. Currently, Phase III studies are being conducted on humans with regard to lung fibrosis, chronic renal failure secondary to kidney glomerulosclerosis, hepatic cirrhosis and breast capsular contracture.

Basic and clinical research works, already published or in process of being published, have shown that pirfenidone lowers the progressive advance of fibrosis lesions. Most importantly, pirfenidone performs said actions in a safe and non-toxic manner. Moreover, it is known that pirfenidone prevents the formation of fibrotic lesions after damage to a given organ, for example liver, skin, kidney, etc.

It is known that one of the mechanisms through which pirfenidone performs its therapeutic effects is through the modulation of the action of several cytokines. Pirfenidone is a potent inhibitor of fibrogenic cytokines and TNF-α. It is well documented that pirfenidone inhibits the excessive biosynthesis and release of several fibrogenic cytokines such as TGF-β1, bFGF, PDGF, and EGF. Zhang S. et al., *Australian and New England J. Ophtalmology* 26:S74-S76 (1998). Other scientific reports also show that pirfenidone blocks the synthesis and liberation of excessive quantities of TNF-α from macrophages and other cells, Cain et al., *Int'l J Immunopharmacology* 20:685-695 (1998).

On the other hand, pirfenidone is a drug that has been applied for restoring tissues with fibrotic lesions and preventing fibrotic lesions as well. This compound, per se, is a known compound and its pharmacological effects have been described, for example, in Japanese applications KOKAI Numbers 87677/1974 and 1284338/1976, as an anti-inflammatory agent that includes anti-pyretic and analgesic effects. U.S. Pat. No. 3,839,346, published on Oct. 1, 1974; U.S. Pat. No. 3,974,281, published on Aug. 10, 1976; U.S. Pat. No. 4,042,699, published on Aug. 16, 1977, and U.S. Pat. No. 4,052,509, published on Oct. 4, 1977, describe methods for obtaining pirfenidone, as well as its use as anti-inflammatory agent. The anti-fibrotic activity of 5-methyl-1-phenyl-2-(1H)-pyridone is described in Mexican patent 182,266.

New applications of pirfenidone have been discovered that are the object of the instant invention, showing that the compound is active in the reduction of the deleterious effects (breast capsular contracture) observed after the surgical implantation of breast implants in humans.

Moreover, as described and illustrated in the instant invention, pirfenidone is also effective in the regression of chronic renal failure secondary to primary human glomerulosclerosis and hepatic fibrosis.

Modern life is characterized by a cult of vanity and self-esteem both for men and women. For this reason, aesthetic surgery is in high demand nowadays. One of the most requested embodiments in aesthetic surgery is breast implant. Although this type of surgery is every day safer, the presence of side or adverse effects is still common. The deleterious effects observed after the placement of the breast implants are inflammation, capsular contracture and fibrosis development. Several materials have been tested for reducing said side effects.

The current beauty concepts have increased the demand for breast surgery for reconstructive and beauty purposes. However, despite the great usefulness of said medical procedure, one of the most frequent complications of post-surgery is the swelling and contracture of the capsule around the implant. Said complications cause malformation, hardness and breast pain deriving in patient's physical and psychological alterations. The causes and histopathogenesis of capsular contracture are not clearly understood. Various publications mention a variable incidence ranging from 0 to 74% (1), depending on the implantation, the type of implant cover, the surface texture and the anatomic site (2) (subglandular or subpectoral). The causes of these complications can be liquid accumulation in the tissue of the implants bag, intense inflammatory response, sub-clinical infection, age of the patient, foreign materials and the alteration of cellular and molecular mechanisms in the implantation area. When an implant is placed, the body reacts encapsulating it and starting a rejection reaction (3.4) with the formation of a hypertrophic scar (5.6). This immune response produces cytokines and growth factors such as IL-1, IL-6, TNF-α, PDGF and TGF-β1 (7, 8). The presence of myofibroblasts in the capsule structure with alpha-SMA (alpha-smooth muscle actin) production has been reported, wherein the most deformed capsules show the highest alpha-SMA production, suggesting that activated myofibroblasts play a direct part in contracture development (8). It has also been shown that the number of fibroblasts present in the tissue is proportional to contracture thickness (9). In order to reduce fibroblasts activation and wound contracture, steroid infiltration in the wound and in the inner part of the implant has been used with minor complications. Said complications are thin skin, fine tissue atrophy, stratification, blue-skin and implant exposition. However, the side effects of steroids and other drugs used are fairly important and their continuous and prolonged use should be avoided.

Pirfenidone (5-methyl-1-phenyl-2-(1H)-pyridone) (PFD) has shown to be efficacious in the prevention of fibrosis formation both in vitro as well as in vivo. It inhibits lung fibrosis (10), peritoneal adherence (11), liver cirrhosis (12, 13), uterine fibromyoma (14), kidney fibrosis (15), keloid scars (16) and delays the development of central nervous system tumors. Pirfenidone can also highly specifically inhibit cytokines such as TNF-alpha, FGF. PGDF and TGF-beta in the human fibroblast blocking the G1 phase of the cellular cycle. Because breast implant induces fibrosis and inflammation and because pirfenidone has shown anti-fibrotic and anti-inflammatory characteristics, the instant invention evidences the effect of pirfenidone in the inhibition of the capsular contracture in breast implant in humans.

Tumor Necrosis Factor-Alpha (TNF-α)

- The TNF protein family includes TNF-α, TNF-β, Fas ligand, CD40 ligand, OX-40, RANK-L (receptor activator of nuclear factor kappa-B ligand) and TRAIL (TNF-related apoptosis inducing ligand).
- For historical reasons it is denominated TNF-α for distinguishing it from TNF-β or lymphotoxin.
- Originally it was identified as a substance present in the serum of animals treated with bacterial endotoxin (lipopolysaccharide or LPS) causing in vivo tumor necrosis (its name is derived from this).
- The main TNF cellular source is activated mononuclear phagocytes although antigen stimulated T lymphocytes. NK lymphocytes and mastocytes can also secrete it.
- TNF is the main mediator of the acute inflammatory response to gram negative bacteria and other infectious microorganisms.
- Its main biological action is to stimulate the attraction of neutrophils and monocytes to the infection zones and to activate said cells for microorganism eradication.
- Mononuclear phagocytes come in two forms: anchored to membrane, and soluble.
- The TNF anchored to membrane form is separated by a membrane associated metalloprotease (MMP-MT) and is released. Three of these polypeptides unite and a TNF circulating protein is formed.
- There are two TNF receptors (TNF-RI and TNF-RII).
- Type I receptor can stimulate the gene expression of inflammatory mediators or induce apoptosis.
- The pro-inflammatory or anti-apoptotic route is initiated by the union of TRADD (TNF Receptor-Associated Death Domain) to the intracytoplasmatic domain of the TNF receptor followed by TRAF-2 (TNF Receptor-Associated Factors) or RIP-1 (Receptor Interacting Protein), leading to NF-kB and Ap-1 dependent gene expression.
- However, if instead of binding to TRAF or RIP it binds to FADD (FAS-Associated Death Domain), this causes apoptosis because it cuts pro-Caspase 8 and said pro-Caspase 8 in turn activates caspase effectors such as Caspase 3, this being the apoptotic route.
- If type II receptor binds directly to TRAF, it causes gene expression of inflammatory mediators.
- The genes induced by TNF receptors code mainly for inflammation mediators and anti-apoptotic proteins.
- Based on the above, use of TNF-α receptor blockers is one of the strategies designed to obliterate inflammatory response.

Thus, in the instant invention it is described and shown that pirfenidone has an extremely potent and selective TNF-α inhibiting action. This information is shown in FIG. 6.

Transforming Growth Factor Beta (TGF-β)

- TGF-β was isolated from human platelets in the 1980's and was identified as a product of cells transformed by the murine sarcoma virus. It was later named transforming growth factor beta for its capacity to cause a phenotypic transformation in an epithelial cells culture because it induced reversible fibroblasts transformation.
- TGF-β main action in the immune system is to inhibit lymphocytes proliferation and activation.
- Outside the immune system, TGF-β is considered the main trigger for the production of extracellular matrix components, inducing fibrosis through the stimulation of the production of collagen type I, III and IV, fibronectin, laminin and proteoglycans. It is increased in hepatic, lung and renal fibrosis both in experimental models as well as in humans.
- It is synthesized as an inactive dimeric precursor.
- Active TGF-β binds to the extracellular domain of type II receptor. Ligand binding promotes TβRII intracytoplasmatic autophosphorylation because of its serine/threonine kinase activity, and in turn TβRII phosphorylates type I receptor, triggering thus Smads (signal transducing intracellular molecules) activation, able to translocate to the nucleus and regulate transcription of target genes such as Smad 7, PAI-I collagen I, PDGF an TGF-β itself.
- Smad2/3-Smad4 complexes in the nucleus can associate with transcription co-activators and co-repressors.
- Three co-repressors are identified for Smad: TGIF protein and two related proteins denominated SnoN and c-Ski. All of them are important repressors of the TGF-β signaling route, although their function in hepatic fibrosis is not fully described.

Thus in the instant invention it is described and shown that pirfenidone has an extremely potent and selective inhibiting action against TGF-β production. This information is shown in FIG. 5.

OBJECTS OF THE INVENTION

One of the objects of the instant invention is to describe a process for manufacturing a pharmaceutical composition in sustained-release tablet form comprising from 600 milligrams to 2400 milligrams of pirfenidone in such a way as to make the drug bioavailable during a prolonged period of time of 12 hours from its administration. Thus, the anti-fibrotic and anti-inflammatory action of the drug pirfenidone is optimized.

A further object of the instant invention is that the administration of sustained-release tablets containing pirfenidone is effective for the regression of chronic renal failure secondary to primary glomerulosclerosis.

A further object of the instant invention is that the administration of sustained-release tablets containing pirfenidone lowers and/or reduces the deleterious effects of breast capsular contracture observed after surgical implantation of breast implants in humans.

Moreover, a further object of the instant invention is the anti-TNF-αr and anti-TGF-β actions of pirfenidone in sustained-release tablets for the treatment of hepatic fibrosis.

The instant invention is illustrated but not limited by the above mentioned objects; moreover its applications as treatment methods and/or pharmaceutical uses in drug preparation together with an acceptable pharmaceutical vehicle for the treatment or regression of chronic renal failure are shown, as well as for the treatment, reduction and/or regression of the deleterious effects in breast capsular contracture and for the treatment of hepatic fibrosis.

BRIEF DESCRIPTION OF THE DRAWINGS

Other features and advantages of the invention will be evident from the following detailed description, the objects and preferred embodiments, the attached claims and the enclosed drawings or Figures, wherein:

DETAILED DESCRIPTION OF THE INVENTION

Figure 1:
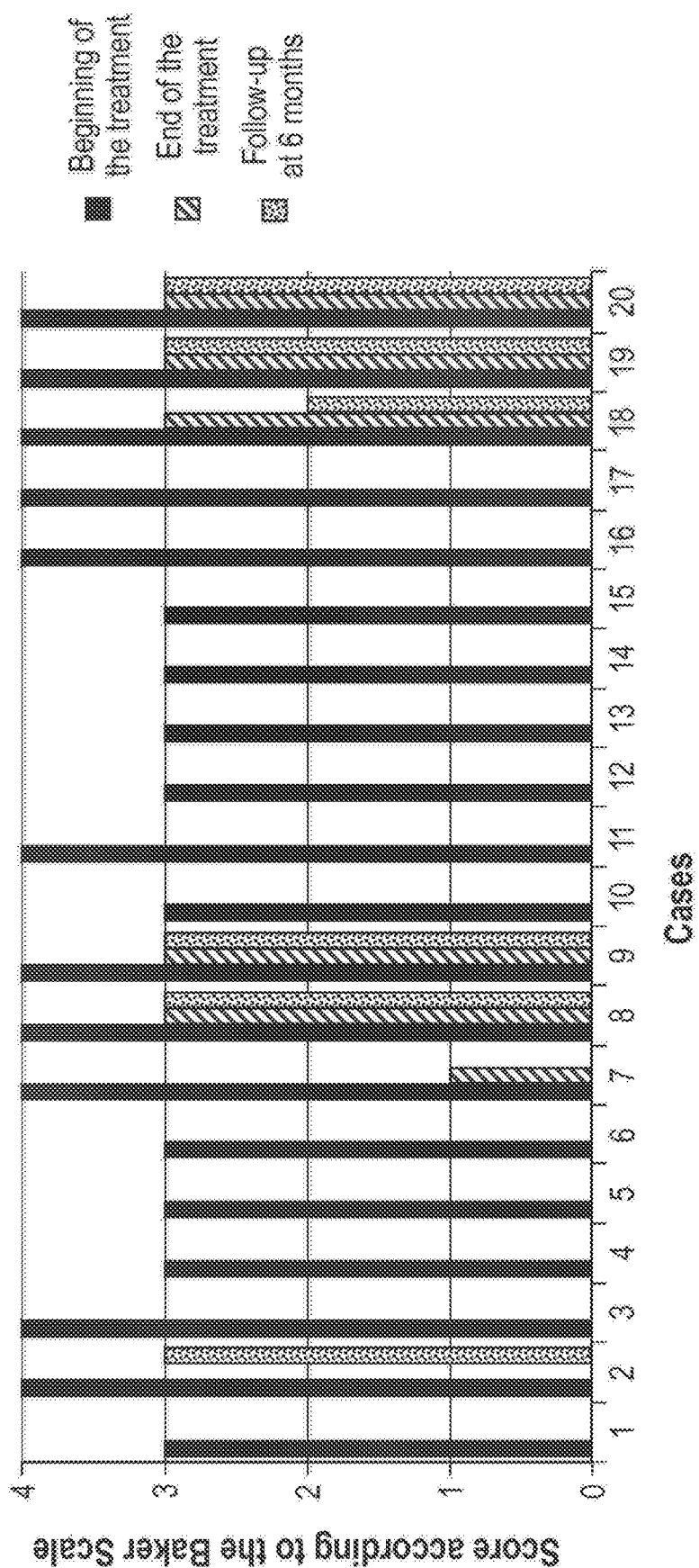
FIG. 1 shows a diagram of breast capsular contracture evolution during the study considering the percentage according to the Baker scale with regard to the number of cases. A comparison between the cases treated with PFD is also shown. All the cases show an important improvement after PFD administration. The six-month follow-up shows only one case of relapse.
Figure 2:
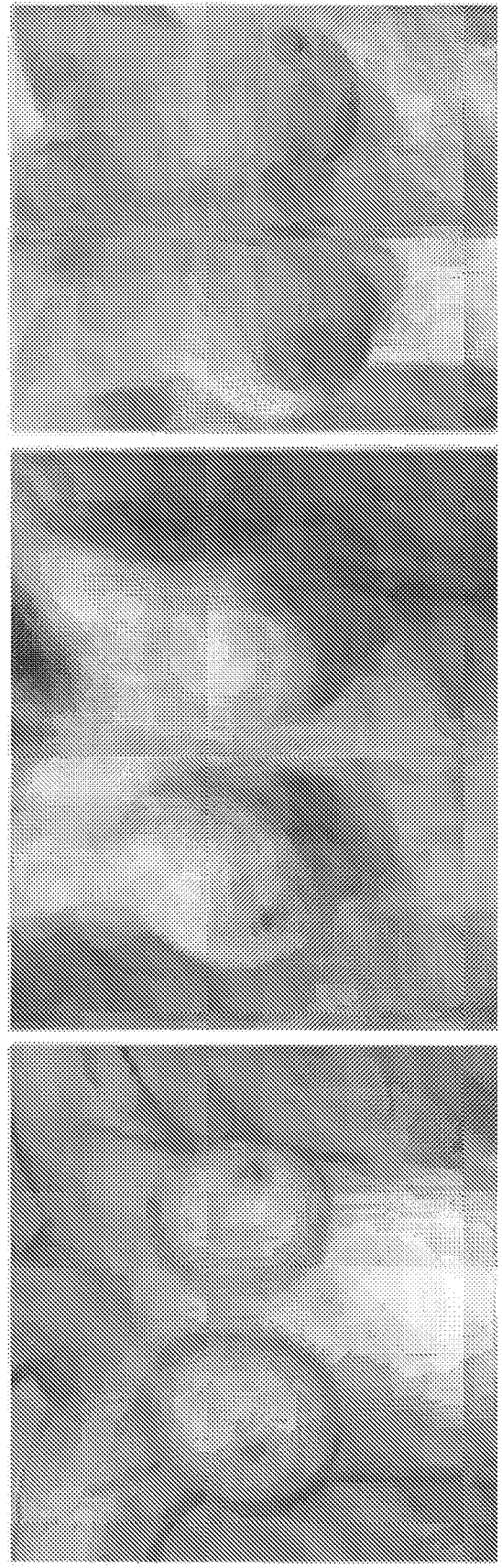
FIG. 2 shows the photograph of a patient with bilateral Breast Capsular Contracture diagnosis. The image on the left hand side shows the right breast with a grade IV contracture and the left breast with a grade Ill contracture; the central picture shows the same patient after six-month PFD administration, in which the left breast shows an improvement to a Not Detectable by Ultrasound or Clinical Examination state, the right breast shows an improvement to grade III. The right panel shows the image obtained at six-month follow-up, in which the lack of relapse is evidenced.
Figure 3:
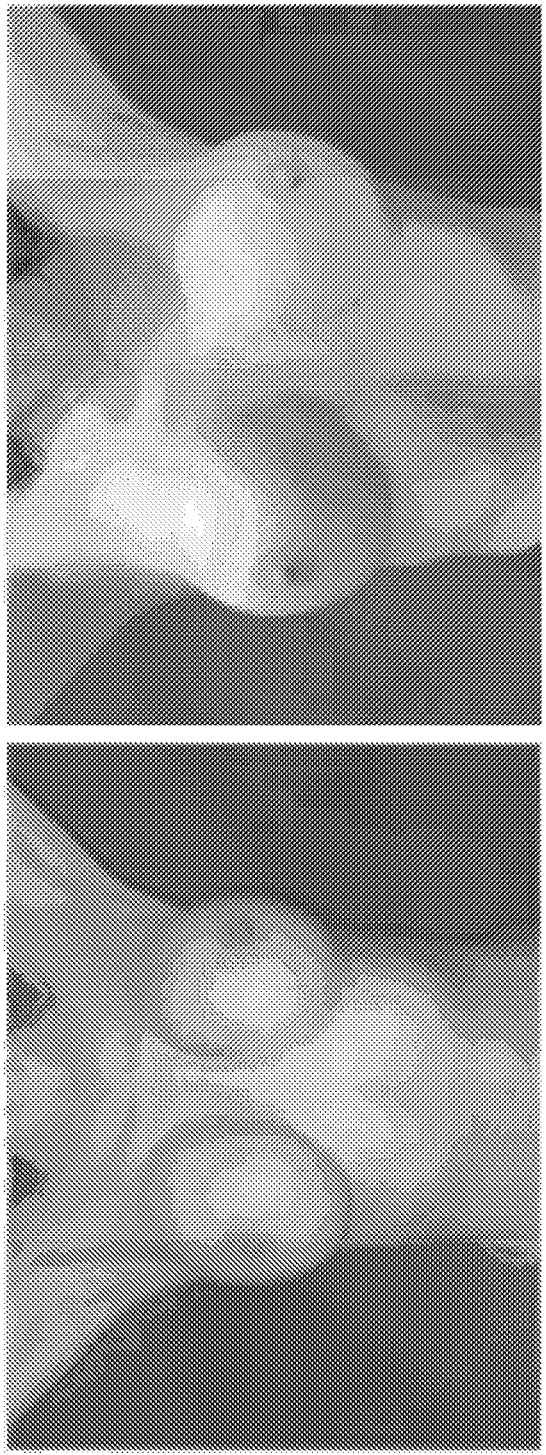
FIG. 3 shows the photograph of a patient with a bilateral Breast Capsular Contracture diagnosis. The image on the left hand size shows a grade IV breast capsular contracture. The image of the right hand side shows the same patient at the end of the protocol with both breasts classified as Capsular Contracture Not Detectable by Ultrasound or Clinical Examination.
Figure 4:
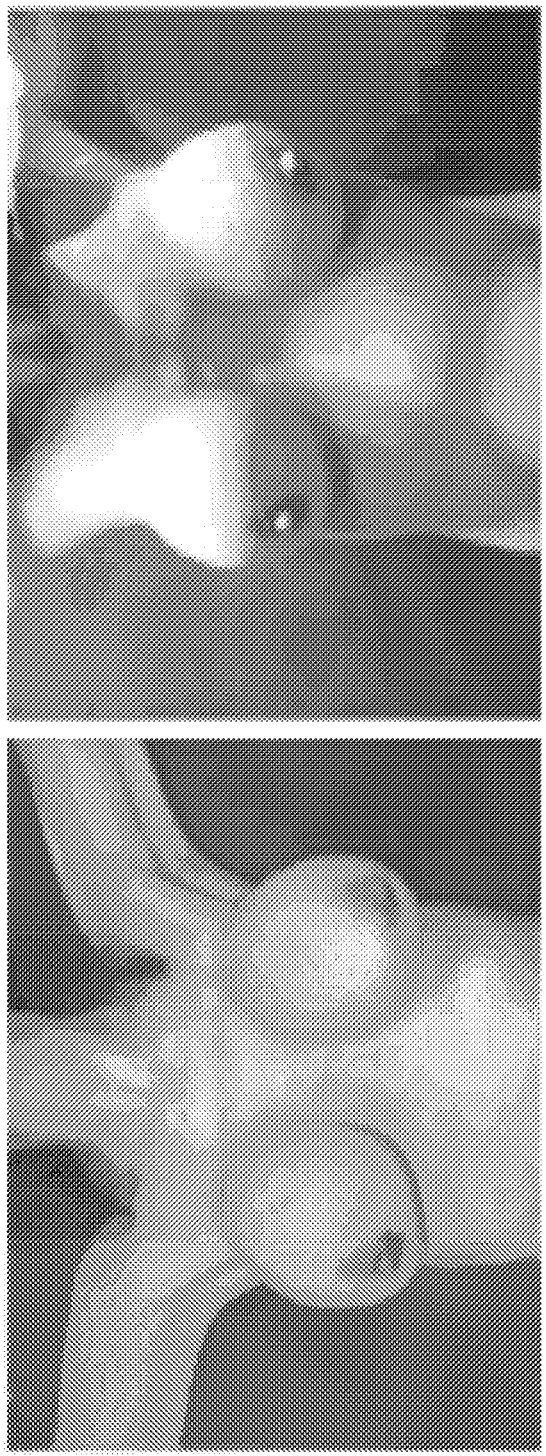
FIG. 4 shows a photograph of a patient with a bilateral Breast Capsular Contracture diagnosis treated with capsulectomy. The image on the left-hand side shows both breasts with grade IV contracture at the time of the evaluation before capsulectomy; the image on the right-hand side shows the same patient at the six-week evaluation after capsulectomy, where a regression of the breast contracture to grade III in the right breast and to grade 11 in the left breast can be observed.

The manufacturing process steps of the tablets in general are described as following.
General process for manufacturing the tablets:
 Order issuance,
 Equipment and area cleaning,
 Supply of raw materials, Powder screening, Granulate mixing, Drying, Final mixing,
 Compression, Blistering, Conditioning,
 Supply of packaging material, and
 PT warehouse.

Although the general tablet manufacturing process is shown above, in the instant invention the detailed process for the manufacturing of a pharmaceutical composition in sustained-release tablet form comprising 600 mg of pirfenidone is detailed, wherein said process comprises the following steps:
Step 1.

Pirfenidone and silicium dioxide are screened through a 30-mesh screen in the oscillating granulator and placed in the ribbon blender and mixed during 5 minutes.

This mixing is performed to obtain a better flow of the active principle because pirfenidone does not show good flow characteristic and silicium dioxide supplies said desired feature because of its anti-adherent properties.
Step 2.

Microcrystalline cellulose, low viscosity hidroxypropylmethylcellulose (HPMC) and high viscosity hidroxypropylmethylcellulose (HPMC) are screened through a 30-mesh screen in the oscillating granulator and placed in the ribbon blender of step 1 and mixed during 15 minutes.

The monocrystalline cellulose is a diluent giving the tablet an appropriate hardness although low compression forces are applied; moreover it contributes to the low brittleness of the tablets. The mixture of low and high viscosity HPMC forms the release matrix; it is made in a mixture ratio appropriate for the slow and steady release of the active principle till its complete release at twelve hours permitting thus a prolonged active principle bioavailability.
Step 3.

Sodium stearyl fumarate is screened through a 30-mesh screen in the oscillating granulator and placed in the ribbon blender of step 1 and mixed during 3 minutes.

Sodium stearyl fumarate is a lubricating agent that prevents the adherence of the tablets on the surface of the punches during tablet formation; moreover it reduces friction between particles.
Step 4.

The granulate obtained is formed in tablets in the stokes tablet making machine equipped with elongated punches having the following compression parameters:

Average weight: 850 mg±5%; Hardness: maximum 10 kgF; Brittleness: below 1%.

Finally, quality control sampling is performed in order to determine if the finished product meets the desired specifications.

Sustained-Release Tablets Comprising 600 mg of Pirfenidone
Quantitative Formula Composition:

| Compound | Quantity |
| --- | --- |
| Pirfenidone | 600.0 mg |
| Microcrystalline cellulose | 118.8 mg |
| Low viscosity HPMC | 70.0 mg |
| High viscosity HPMC | 46.5 mg |
| Silicium dioxide | 8.5 mg |
| Sodium stearyl fumarate | 6.2 mg |

Pirfenidone Bioavailability Study in Healthy Volunteers According to the Pharmacopoeia Standards In this study with 11 healthy volunteers, it was shown that the bioavailability of this drug in 600 mg sustained-release tablet form is prolonged till 12 hours and blood effective therapeutic concentration was determined according to the pharmacopoeia standards. Said analyses were performed by a laboratory authorized by the Mexican Health Secretariat (Data not shown).

Maximum concentration data evidenced that the bioavailability is extrapolated to other lower concentrations, i.e., 100, 200 or 400 mg.

Application of Sustained-Release Tablets Containing Pirfenidine in the Regression of Chronic Renal Failure Although diabetic nephropathy is the main cause of terminal renal disease after the fourth decade of life, in the young adult there are other causes that are in some way the continuity of infants and adolescent pathologies, so that the population under 40 years of age in need of functional replacement through dialysis and transplant most frequently relates to primary or secondary glomerular diseases. The first cause of terminal renal disease under 16 years of age is primary glomerular diseases many of which are diagnosed at a late stage when they have already caused severe renal structural damage, i.e., damaged over 60% of the nephron population and unfortunately manifest themselves in advanced phases of renal failure. The earliest manifestation of a primary glomerular disease is constituted by proteinuria documented, in most of the cases, as "nephrotic syndrome", this generally progressive finding being usually followed by systemic arterial hypertension and, finally, progressive functional failure.

Several mechanisms are responsible for damage progression, one of them being intraglomerular hypertension and hyperfiltration, initiating a disorderly response that induces glomerular sclerosis and nephron destruction. The increase of intraglomerular hydrostatic pressure can cause an increase of mesangial cell contraction and a production increase of TGF-$\beta$, and various cytokines and growth factors.

They include vasoactive agents such as angiotensin II, thromboxanes, endothelin-1 and type IL-1 and TNF-$\alpha$ cytokines.

It is currently considered that massive and persistent proteinuria per se is an independent factor contributing to the progression in all the forms of chronic renal disease. The excess of protein filtration within the proximal tubule and its subsequent endocytosis can represent a pathological mechanism in the renal fibrosis development. A possible scenario for explaining the relationship between proteinuria grade and progression to renal failure can be related to the tubular epithelial cells that, upon endocyting proteins, activate and over-express chemotactic factors such as monocytes (MIP-1), promoting the infiltration of mononuclear cells, among them macrophages that are a rich source of TGF-$\beta$ promoting the phenotypic change of fibroblasts in myo-fibroblasts, increasing thus the extracellular matrix synthesis and type I and III fibrillar collagen deposits contribute to the interstitial fibrosis.

The severity of this deposit lowers thus the glomerular filtration rate.

Based on the above exposed mechanisms, strategies have been used in the past years to try to reduce said deleterious factors, such as:

Low-protein diets for reducing hyperfiltration and concomitant drugs such as Inhibitors of Angiotensin-Converting Enzyme (Enalapril, Lisinopril), or Angiotensin Receptors Antagonists II (Sartanes), that lower intraglomerular hypertension and thus considerably reduce proteinuria, mechanisms that are responsible for the damage.

Direct Background

For logical reasons, the use of an anti-fibrotic agent, especially if it lowers TGF-$\beta$ and TNF-$\alpha$ expression, will be useful for the treatment of patients in the initial phases of glomerular nephropathy. This will detain the progressive and continuous deterioration observed in these patients and prevent early transplantation need.

In animal models, it has been shown that pirfenidone:
Can prevent the development of progressive renal disease.
Reduces proteinuria levels.
Reduces urea nitrogen and serum creatinine levels.
Improves renal function reducing collagen accumulation in the renal cortex.
It also reduces TGF-$\beta$ expression.

The animals treated with pirfenidone grew and developed normally and without toxic effects.

Pirfenidone is an anti-fibrotic agent that has shown to be effective in vitro or in vivo for the prevention and resolution of the accumulation in experimental models of:
Pulmonary fibrosis
Renal fibrosis
Hepatic fibrosis.

The use of the drug in humans has had the same objective focused onto different apparatus and systems. Two reports from 2003 and 2006 of a study conducted by Dr. Armendariz et al present the results obtained with pirfenidone in patients with hepatic fibrosis. Said study has currently been expanded to a larger population and has shown beneficial effects as evidenced through hepatic biopsy.

On the other hand, a study was conducted on renal failure patients treated with hemodialysis and having a history of sclerosing peritonitis. Drug pharmacokinetics was evaluated in said patients. The study showed that it is not necessary to adjust the pirfenidone dose in patients with renal damage and that pirfenidone is well tolerated by patients with Terminal Chronic Renal Failure (TCRF) without showing significant side effects.

Pirfenidone was also evaluated by Cho Me et al in 2007 on patients with nephrotic syndrome and focal segmental glomerulosclerosis in order to delay renal function impairment, obtaining favorable results. The Institute for Renal Digestive and Diabetes Diseases as well as the Institute of Health of the United States of America gave information regarding the use of pirfenidone in two studies authorized by the FDA, one of them on patients with focal segmental glomerulosclerosis in various stages of renal damage and the second on patients with diabetic nephropathy.

Rationale

It is important to take into account that the expensive chronic renal failure (CRF) has become a red spot in Mexico because of its growth rate (11%). Appropriate public health policies must be established in order to absorb the future costs of this unavoidable problem. The public health system offers renal replacement (dialysis) therapies to some 70,000 patients, but it is calculated that for each patient receiving attention, there are two non treated persons. Because of the lack of resources, if this growth rate continues, only one out of four patients will have access to therapy.

For this reason, in pharmacoeconomic terms, the implementation of new therapeutic strategies, such as the one described herein, has enormous relevance.

Renal damage and its progression can be studied through laboratory methods focused onto measuring proteinuria magnitude, renal function evaluated through creatinine clearance, reciprocal creatinine (1/creatinine) and cystatin C and with Doppler ultrasound comparative findings in which anatomical, echosonographic, corticomedular changes as well as flow rate in different renal areas and resistance indexes can be observed; finally, the golden rule to evaluate the magnitude of the damage is the hystological study that expresses the affected structures and the fibrosis extension. Not all these studies can be conducted routinely, because renal biopsy is an invasive procedure that can only be justified reiteratively in patients already submitted to a first procedure for results comparison purposes. On the other hand, laboratory and office methods can be conducted with a defined chronogram.

Study Design

The present study is a prospective, open label, 12-month clinical trial including 30 patients with primary nephropathy, with renal damage (stages 1 to 4 of the KDIGO Classification) between 10 and 40 years of age, from both sexes. All the patients were observed with regard to their evolution by means of laboratory examinations at least three months before their inclusion into the study. Said evaluation phase was useful so that the patient could become his/her own control.

All of the patients received oral Pirfenidone (in sustained-release tablet form) administered every 12 hours containing 2400 mg/1.73 m$^2$ BSA, equivalent to 1400 mg/m$^2$ BSA/24 hrs.; besides, they also received a conventional treatment appropriate for primary nephropathy and CRF, such as antihypertensives, alpha-ketoanalogues, phosphate chelating agents, angiotensin II antagonist, low-protein diet, etc.

They were evaluated every two months during the first six months, and then at 9- and 12-month follow up with laboratory determinations including cystatin C value and creatinine clearance, reciprocal creatinine and proteinuria in 24-hour collection. Two Doppler ultrasonographic studies were performed on each patient at the beginning of the study and at 12 months. Drug adverse events were evaluated and the loss of renal function and loss percentage were quantified.

Experimental Evidence/Results

Taking into account the above, a study was conducted with a patient population having renal damage diagnosis evidenced through laboratory or office methods as common denominator and wherein the use of Pirfenidone at therapeutic doses calculated per m$^2$/Body Surface Area was useful for delaying or modifying renal damage.

Pirfenidone influenced positively renal damage progression rate (phases 1-4 according to KDIGO classification) in patients with chronic renal failure secondary to primary nephropathy.

The use of Pirfenidone in renal function was monitored through cystatin C, plasma reciprocal creatinine and creatinine clearance in 24-hour urine collection.

Moreover, the beneficial effect of Pirfenidone on proteinuria was determined and it was evidenced, through the analysis of the comparative ultrasonographic changes at the beginning and the end of the treatment, that Pirfenidone detains the histological damage to the affected kidneys.

A very important observation of the study and THE FIRST OF ITS KIND was the fact that the drug side-effects on patients with primary nephropathy were limited to a minimum percentage of patients and disappeared rapidly.

Application of Sustained-Release Tablets Containing Pirfenidone in the Regression of Breast Capsular Contracture Currently, breasts play an important part in women sensitivity and constitute a femininity symbol. For this reason, in the last few years, women have found in surgery an important ally to increase the size or improve the aspect of their breasts, either for aesthetic or reconstructive purposes. In the past, several attempts were made to increase the size of breasts, using various injected or implanted materials, including elements of the body itself (1895. Czerny) such as gluteal adipose tissue. However, most of them generated complications leaving hard, painful breasts that did not have the expected shape. In 1963, Cronin and Gerow introduced the silicone implant and since that time it has been possible to obtain good results consistently (17, 18).

However, there are some risks related to this surgery. Some complications may occur after the surgery, such as infection, edema, hemorrhage, pain, slow or poor scarification, anesthetic reaction, hypoesthesia, change of the position of the implant, and most frequently, capsular contracture. This causes firmness, pain and, in severe cases, some external deformation can be seen (19, 20).

The causes and pathogenesis of capsular contracture are not clearly understood. Several publications mention a variable incidence of capsules from 0% to 74% (1), depending on the type of implant, the surface (textured or smooth), and the implantation or anatomic site (subglandular or subpectoral) (2). The causes of these capsules could be the accumulation of liquid in the breast implant bag tissues, intense inflammatory response, subclinical infection, the age of the patient, materials and the alteration of cells and molecular mechanisms in the implantation zone.

When an implant is placed, the organism reacts encapsulating the foreign body from a rejection (3-6). This immune response is mediated by cytokines and growth factors such as interleukin-1 (IL-1), IL-6, tumor necrosis factor-$\alpha$ (TNF-$\alpha$), platelets from the derived growth factor, and transforming growth factor-$\beta$1 (TGF-$\beta$1) (7, 8). The presence of myofibroblasts in the contractured capsule has been reported always together with the production of $\alpha$-smooth muscle-actin ($\alpha$-SMA); the most deformed capsules showing a larger production of $\alpha$-SMA, suggesting a direct function of myofibroblasts activity in the development of the contracture (8). It has also been evidenced that the number of myofibroblasts present in the tissue is proportional to the thickness of the Contractured Capsule (9). The above data were obtained with human beings.

On the other hand, various studies have used animal models of mammary capsular contracture post-placement of mammary implants. Animals such as pigs, rabbits, rats, mice have been used with variable results. Some animal models imply the addition of an implant inducing agent in order to accelerate the development of the contracture. All of them show fibrosis development, fibroblast activation, inflammation and thickness of mammary capsule (21-27).

In prior studies using rabbits and mice models, the pre-instillation of the implant bag with sodium 2-mercaptoethane sulphonate (mesna) and mitomycin C reduced the thickness of the capsule, lowered the number of fibroblasts and reduced collagen deposit (21, 22). However, said drugs are not commonly used currently in clinical practice. In order to reduce fibroblast activation and wound retraction, the infiltration of steroids on the wound and inside the implant has reported few complications. Steroids are not frequently used currently and are not recommended by implant manufacturers. Complications include skin thinning, tissue atrophy, striations, blue-colored skin, and implant exposition (28-36).

Direct Background

Pirfenidone (5 methyl-1-phenyl-2-[1H] pyridone) (PFD), a new antifibrotic agent, has shown to be efficacious both in vitro as well as in vivo, preventing and eliminating fibrous tissue in experimental models of pulmonary fibrosis (10), peritoneal adherences (11), experimental and human hepatic cirrhosis (12, 13), uterine fibromas (14), renal fibrosis (15), and scars (16). Moreover, PFD can inhibit fibroblast growth factor and TGf-$\beta$1 produced by human fibroblasts.

On the other hand, it has been evidenced that Pirfenidone administered orally in female rats with silicone implants in mammary gland prevents the development of the characteristic fibrosis in the mammary capsule that finally causes the painful contracture (Matfas Gancedo, Aesthetic Plastic Surgery 2008).

Because mammary implants induce fibrosis and inflammation and PFD has shown anti-fibrotic and anti-inflammatory properties in different pathologies and organs, one of the main objects of this invention is to determine the pharmacological properties of oral Pirfenidone in the post-surgery evolution of patients after the placement of mammary implants. The study was focused on the reduction of the thickness of the Periprosthetic Capsule and/or prevention of its thickening and on the prevention of the recurrence of capsular contracture.

The use of breast implants is related to complications such as Capsular Contracture (CC). This is defined as the thickening of the capsule surrounding the implant and is classified from Grade I to grade IV (Baker Scale) according to texture, implant visibility and deformity and shows an incidence ranging from 15 to 45%. Table 1. Baker Scale.

TABLE 1

BAKER SCALE

|  | FIRMNESS | IMPLANT PALPATION | IMPLANT VISIBILITY |
|---|---|---|---|
| GRADE I | Slight | Not palpable | Not visible |
| GRADE II | Minimum | palpable | Not visible |
| GRADE III | Moderate | Easily palpable | Distortion |
| GRADE IV | Severe | Hard, painful and cold | Severe distortion |

Prior studies, both in human as well as in animal models have been used for evidencing new therapeutic embodiments for Breast Capsular Contracture. Unfortunately, most of these therapies do not generate a significant response and show a high relapse rate.

For medical research and drug development, the use of single nucleotide polymorphisms (SNPs) has been very useful. They do not vary much from one generation to the other and can be evidenced through genetic markers. A genetic marker is a DNA segment with a physical location identifiable on a chromosome.

It has been determined that Capsular Contracture appears partly as an immune response mediated by cytokines and growth factors such as Transforming Growth Factor-B1 (TGF-β1).

Rationale

The object of this study is to offer another therapeutic focus to breast capsular contracture in order to implement a treatment that reduces or eliminates the use of drugs or surgical procedures (capsulotomy, capsulectomy) described up to now for its management, obtaining a lower relapse rate and improving thus the patient's quality of life.

Study Design

It is a pilot, open, prospective, longitudinal and analytical essay in which 17 patients diagnosed with an important breast capsular contracture (Grade III and Grade IV, Baker Scale) were treated with Pirfenidone 600 mg administered orally as sustained-release tablets three times per day (every 8 hours) during six months.

A blood sample was taken from each patient in order to determine the genetic markers (TGF-β1). Using PCR-RFLP, three Breast echosonographies were made, one at the beginning, the other at the end of the treatment (6 months) and the last one 6 months after the suspension of Pirfenidone treatment (12 months). Two parameters were evaluated: antero-posterior diameter and capsular thickness in all its quadrants (contrasting thickness measurements with the radiological parameters established by Tomas Stavros, 2006 and the radiological clinical correlation of thickness vs Baker Scale established by Alon Zahavi M D, 2006 for the diagnosis of Capsular Contracture). Free liquid in the capsule was looked for, as well as retraction or rupture signs through 5-12 MHz linear or curve transductors.

During 12 months, a Breast Clinical Evaluation was also conducted on a monthly basis using Baker Classification. Deformation, texture through palpation and sensitivity were evaluated. A registration of each evaluation was made with digital photographs. The clinical and radiological changes of each breast were evaluated by a plastic surgeon and a qualified radiologist.

The statistical analysis included 20 cases, taking into account that 3 patients presented bilateral capsular contracture of different grade in each breast; a total of 20 breasts were analyzed.

The protocol was approved by the regulatory authorities and the Ethic Committee of the Instituto Jalisciense de Cirugía Reconstructiva "Dr. José Guerrero Santos", registration number 01/09. All the patients signed an informed consent at the beginning of the protocol. Besides, this study was conducted according to the Helsinki Declaration and according to the local legislation and regulations applicable to the use of a new therapeutic agent in Mexico.

Experimental Evidence/Results

All the cases included in the study showed a reduction of breast capsular contracture grade. In 70% of the cases (n=14), it concluded Without Clinical or Sonographic Evidence of Capsular Contracture (WCSECC). Among these cases, 9 (45%) were grade III and 5 cases (25%) were grade IV. The remaining 30% corresponded to grade IV cases that only reduced capsular contracture; 1 case (5%) from grade IV to grade II and 5 cases (25%) from grade IV to grade III.

Importantly, the 6-month follow up after Pirfenidone discontinuation showed that ONLY 1 case (5%) grade IV showed relapse of capsular contracture from WCSECC to grade III at the end of the study because of the use of steroids and excessive exercise.

It has to be emphasized that all the patients presenting grade III (9 cases [45%]) responded to the pirfenidone treatment ending the study Without Clinical or Sonographic Evidence of Capsular Contracture (WCSECC) (p<0.001, according to the Wilcoxon matched-pairs signed-ranks); (Table 2).

TABLE 2

Capsular contracture grade relationship according to Baker Scale; at the beginning, at 6 months and at the end of the study with Pirfenidone

| Contracture Grade | WCSECC ** | I | II | III | IV | Cases |
|---|---|---|---|---|---|---|
| Initial | — | — | — | 9 | 11 | 20 |
| 6 Months | 10 | 5 | — | 5 | — | 20 |
| 12 months | 14 | — | 1 | 5 | — | 20 |

\* p < 0.001 Wilcoxon matched-pairs signed-ranks and chi$^2$
\*\* WCSECC *Without Clinical or Sonographic Evidence of Capsular Contracture.* According to Alon Zahavi, MD and Stavros, MD.

The echographic findings corresponded to breast capsular contracture diagnosis, reporting an increase in the antero-posterior diameter of the capsule thickness, presence of intracapsular liquid and retraction data before the start of the Pirfenidone treatment.

A gradual reduction of the antero-posterior diameter (APD) and capsule thickness was obtained in 19 cases (95%) as evidenced through the echographies conducted at 6 and 12 months. A Student's t analysis was applied for paired samples; upon analyzing the APD a P value ≤0.001 was obtained contrasting the beginning and 6-month values; and a P=N. S, was obtained contrasting the 6-month and 12-month values (Table 3). In the capsule thickness comparison between quadrants. P was significant in each case as shown in Table 4. It has to be emphasized that the only case of contracture relapse (5%) showed an increase of said parameters in the sixth- to twelfth-month period.

Two cases (10%) in the patient group that passed from grade IV to grade III showed retraction data and light subcapsular liquid at the end of the study.

TABLE 3

Comparison of the Antero Posterior diameter (APD) of the breast implant, echographically measured at the beginning, at 6 months and at 12 months.

|   | Initial AP Diameter* | AP Diameter* at 6 months | AP Diameter* at 12 months |
|---|---|---|---|
| $\bar{x}$ | 7.57 | 6.425 | 6.085 |
| σ | 2.159 | 2.319 | 2.062 |
| T |  | $P \leq .001$ | $P = N.S.$ |

*Values expressed in centimeters.
T for related samples; $\bar{x}$ (Mean) and σ (Standard Deviation).

TABLE 4

Comparison of the capsule thickness at the beginning and at the end of the study per quadrant. **

|   | Implant fibrous capsule OUQ | | Implant fibrous capsule IUQ | | Implant fibrous capsule OLQ | | Implant fibrous capsule ILQ | |
|---|---|---|---|---|---|---|---|---|
|   | Beginning | End | Beginning | End | Beginning | End | Beginning | End |
| $\bar{x}$ | 1.505 | 1.18 | 1.6 | 1.19 | 1.775 | 1.185 | 1.86 | 1.115 |
| σ | 0.464 | 0.472 | 0.681 | 0.518 | 1.062 | 0.474 | 1.280 | 0.446 |
| T | $P = .001$ | | $P = .001$ | | $P \leq .005$ | | $P \leq .01$ | |

* Values expressed in centimeters.
** OUQ (Outer Upper Quadrant), IUQ (Inner Upper Quadrant), OLQ (Outer Lower Quadrant), ILQ (Inner Lower Quadrant) + capsular Contracture = Capsule Thickness ≥1.5 mm according to Stavros, and 1.42 mm according to Alon Zahavi. T for related samples; $\bar{x}$ (Mean) and σ (Standard Deviation).

The SNP genetic analysis for TGF-β1 (Table 5) showed that 15 of the patients (88.2%) were homozygous G/G for the genotype (codon 25; 25/Arg25 genotype Arg) and 2 patients (11.8%) were heterozygous G/C TGF-β1 for the genotype (codon 25; 25/Arg25 genotype Arg). From this it was determined that the patients with G/G genotype have a higher probability of developing breast capsular contracture.

TABLE 5

Table 5. Genotypic frequencies and allelic distribution of polymorphism TGF-β1 Arg25Pro in patients in the Breast Capsular Contracture Group and in the Control Group with breast implant.
TGF-β1 (Arg25Pro)

|   | Patients with breast Capsular Contracture (n = 30) | | Control Group | |
|---|---|---|---|---|
|   | Group treated with PFD (n = 17) Frequency (%) | Group treated with capsulectomy (n = 13) Frequency (%) | (n = 30) Control group with breast implant Frequency (%) | $p^1$ |
| Genotype | | | | |
| G/G | 15 (88) | 13 (100) | 5 (17) | 0.0001 |
| G/C | 2 (12) | 0 (0) | 25 (83) | |
| C/C | 0 (0) | 0 (0) | 0 (0) | |
| Allele | | | | |
| G | 32 (94) | 26 (100) | 35 (58) | |
| C | 2 (6) | 0 (0) | 25 (42) | |

Side effects such as stomach aches, fatigue, skin dermatosis and photosensitivity were only present in 6 patients (35%6), with a mean of 10.8 days.

Finally, the statistical analysis of the ordinal scale variables was conducted with means and ranges; and for the contrasts, Wilcoxon matched-pairs signed-ranks and $Chi^2$ were used. With regard to the Ratio Interval variables, the mean and standard deviation were used; and for the contrast, Student's t test for paired samples was used in which a case is compared against another case. Table 6 summarizes integrally said comparative analysis.

TABLE 6

Table 6. Comparison of Breast Capsular Contracture at the beginning and at 12-month follow up in both groups.
BAKER SCALE

| GROUP | Beginning of the study Mean (Range) | 12-month follow-up Mean (Range) | P** |
|---|---|---|---|
| PFD (n = 20) | 4 (3-4) | 0.5 (0-3) | 0.0001 |
| CAPSULECTOMY (n = 14) | 4 (3-4) | 2 (1-3) | 0.001 |
| P* | NS | ≤0.006 | |

Table 6. Results of the statistical analysis between the study groups.
*U de Mann-Whitney.
**Wilcoxon for paired samples.
NS = no Significant.

Pirfenidone Anti-TNF-α and Anti-TGF-β1 Action in Sustained-Release Tablets

Pirfenidone, prepared according to the previously described quantitative formula for extended release and before conversion into tablets, was used for conducting the experiments described hereinafter in order to demonstrate its anti-TNF-α and anti-TGF-31 action.

Basically. Pirfenidone efficacy at inducing fibrosis regression, both at experimental level as well as at human treatment level is supported by its inhibitory action against TNF-α and TGF-β synthesis and production.

It is essential to highlight that it has been demonstrated both in vitro as well as in vivo that Pirfenidone selectively inhibits NF-kβ, lowering dramatically the activation of genes codifying for pro-inflammatory proteins (TNF-α and TGF-β1).

Experimental Evidence/Results

Figure 5:
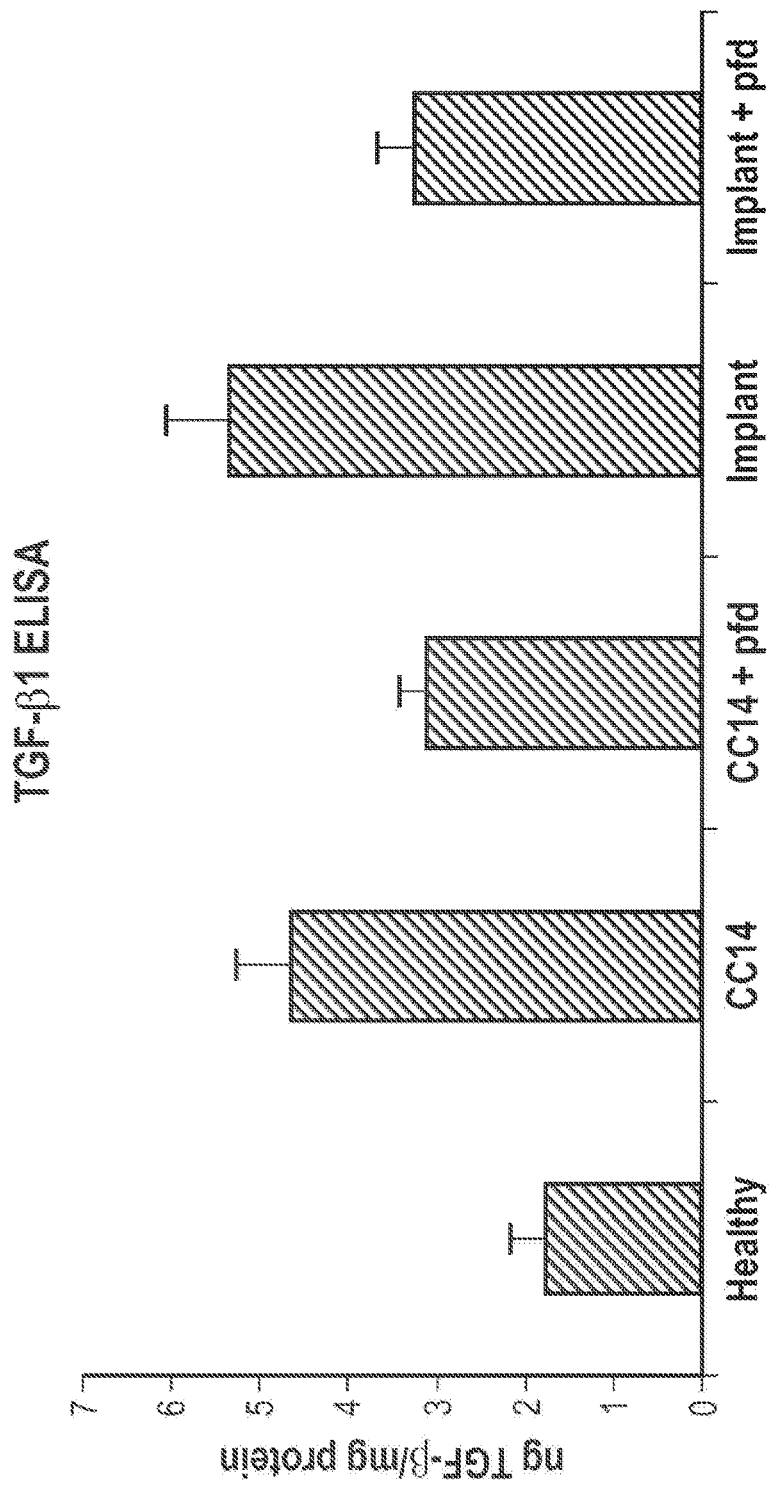
FIG. 5 shows a diagram with TGF-β1 serum levels determination in female rats submitted to the placement of silicone implants in mammary glands for inducing contracture development.

TGF-β1 serum levels determination in female rats submitted to the placement of silicone implants in mammary glands for inducing contracture development are shown in FIG. 5. The animals were administered a daily regimen of oral Pirfenidone during 21 days. In the same diagram it can be seen that also animals with chronic hepatic damage by hepatotoxic CCl4 (Carbon Tetrachloride) have a lower TGF-β1 serum level when treated with Pirfenidone. TGF-β1 levels were determined through a commercial ELISA kit.

Figure 6:
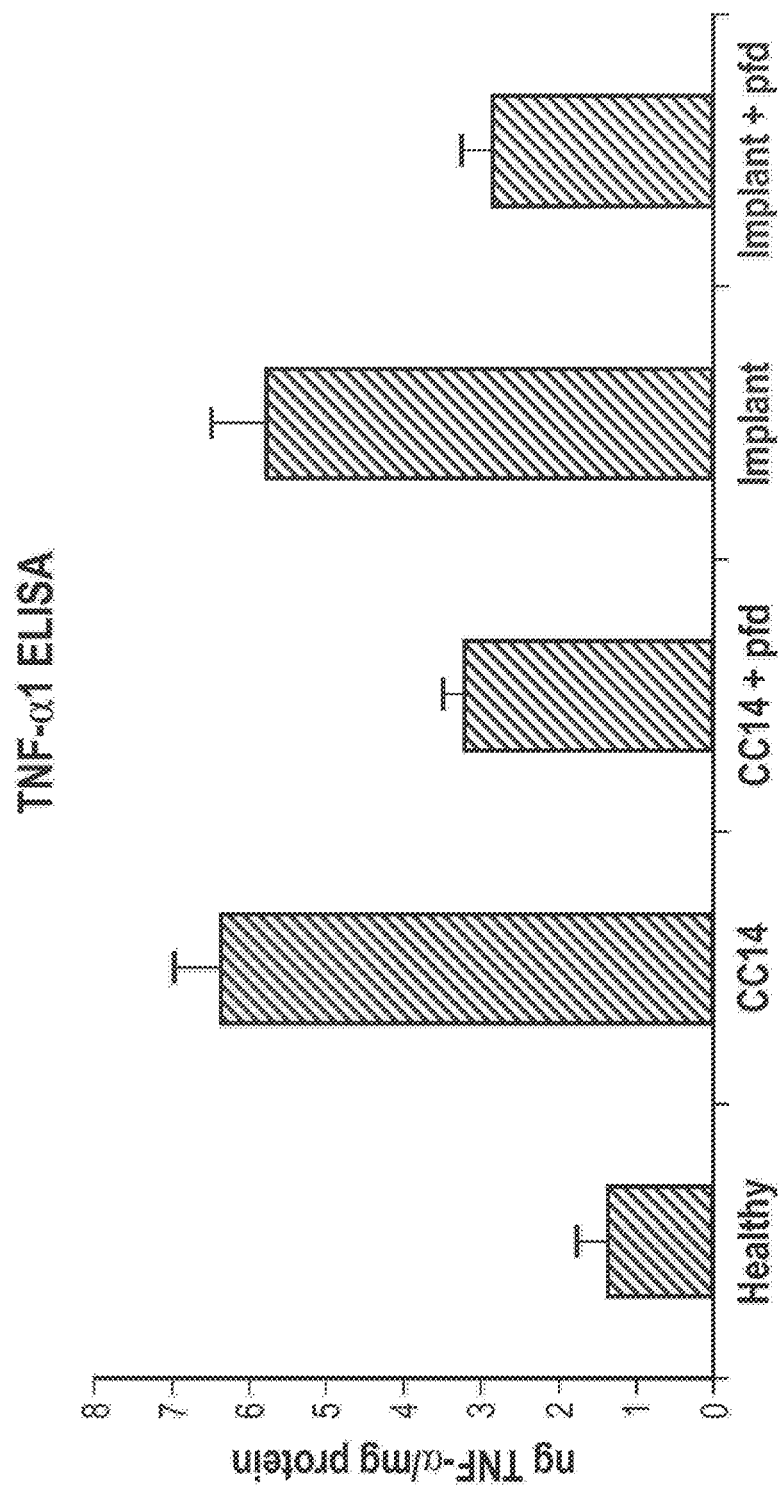
FIG. 6 shows a diagram with TNF-α serum levels determination in female rats submitted to the placement of silicone implants in mammary glands for inducing contracture development.

TNF-α serum levels determination in female rats submitted to the placement of silicone implants in mammary glands for inducing contracture development are shown in FIG. 6. The animals administered a daily regimen of oral Pirfenidone during 21 days. In the same diagram, it can be seen that also animals with chronic hepatic damage by CCl4 have a lower TNF-α serum level when treated with Pirfenidone. TNF-α levels were determined through a commercial ELISA kit.

REFERENCES

1. Burckhardt B R (1988) Capsular contracture: Hard breasts, softdata. Clin Plast Surg 15:521
2. Collins N. Coleman D, Foo I T H, Sharpe D T (2000) Ten years of a prospective randomised controlled trial of textured versus smooth subglandular silicone gel breast implants. Plast Reconstr Surg 106:786-791.
3. Vistnes L M, Ksander G A, Kosek J (1978) Study of encapsulation of silicone rubber implants in animals: A foreign body reaction. Plast Reconstr Surg 62:580-588
4. Coleman D J, Foo I T H, Sharpe D T (1991) Textured or smooth implants for breast augmentation? A prospective controlled trial. Br J Plast Surg 44:444-448
5. Lossing C. Hanson H A (1981) Peptide growth factors and myofibroblastin capsules around human breast implants. Plast. Reconstr Surg 91:1277-1286
6. Vistnes L M, Ksander G A, Isaacs G, Rozner L (1981) Elevated glycosaminoglycans and chondroitin 4-sulfate and other properties of contracted human prosthesis capsules. Ann Plast Surg 7:195-203.
7. Kuhn A. Sing S, Smith P D (2000) Periprosthetic breast capsules contain the fibrogenic cytokines TGF-□1 and TGF-□2, suggesting possible new treatment approaches. Ann Plast Surg 44:387-391.
8. Brohim R M. Foresman P A, Hildebrandt P K (1992) Early tissue reaction to textured breast implant surfaces. Ann Plast Surg 28:354.
9. Lossing C. Hansson H A (1993) Peptide growth factors and myofibroblasts in capsules around human breast implants. Plast Reconstr Surg 91:1277-1286.
10. Iyer S N, Wild J S, Schiedt M J, Hyde D M, Margolin S B, Giri S N (1995) Dietary intake of pirfenidona ameliorates bleomycin induced lung fibrosis in hamsters. J Lab Clin Med 125:779-785.
11. Al-Took S, Murray C. Tulandi T (1998) Effects of pirfenidona and dermoid cyst fluid on adhesion formation. Fertil Steril 69:341-342.
12. Garcia L, Hernández I, Sandoval A, Salazar, Garcia J, Vera J, Grijalva G, Muriel P, Margolin S, Armendariz-Borunda J (2002) Pirfenidone affectively reverses experimental liver fibrosis. J Hepatol 32:797-805.
13. Armendáriz-Borunda J, Islas-Carbajal M C. Meza-Garcia E. Rincón AR, Sandoval A S. Salazar A. Berumen J. Álvarez A. Covarrubias A, Aréchiga G. García L (2006) A pilot study in cirrhotic patients using a new antiinflammatory and antifibrotic agent, pirfenidone. Gut 55:1663-1665.
14. Lee B-S, Margolin S B, Nowak A R (1998) Pirfenidona: A novel pharmacological agent that inhibits leiomyoma cell proliferation and collagen production. J Clin Endocrinol Metab 83:219-223.
15. Shimizu T, Kuroda T. Hata S. Fukagawa M, Margolin S B. Kurokawa K (1998) Pirfenidone improves renal function and fibrosis in the postobstructed kidney. Kidney Int 54:99-109.
16. Shetlar M R. Shetlar D J. Bloom R E. Shetlar C L. Margolin S B (1998) Involution of keloid implants in athymic mice treated with pirfenidone or with triamcinolone. J Lab Clin Med 132:491-496.
17. Porras-María. Tratamiento fisioterapéutico de la contractura capsular después de mamoplastía de aumento. Revista Colombiana de Cirugía Plástica. http://www-.medilegis.com/bancoconocimiento/R/Rev_cirugiaN3dic_contractura/artic ulocontractura.htm.
18. http://es.wikipedia.org/wiki/Aumento_de_pecho, la Fundación Enciclopedia Wikimedia Project.
19. http://es.wikipedia.org/wiki/Aumento_de_pecho, la Fundación Enciclopedia Wikimedia Project.
20. F. J. Escudero, y colb. Reacción Tisular a la Prótesis Mamaria. Contractura Capsular Periprotésica. An Sist. Sanit. Nanar, 2005; Vol. 28 (Suplemento 2): 41-53.
21. Ajmal N, Riordan C L, Cardwell N, Nanney L B, Shack R B (2003) The effectiveness of sodium 2-mercaptoethane sulfonate (MESNA) reducing capsular formation around implants in a rabbit model. Plast Reconstr Surg 112:1455-1461.
22. Frangou J. Kanellaki M (2001) The effect of local application of mitomycin C on the development of capsule around silicone implants in the breast: An experimental study in mice. Aesth Plast Surg 25:118-128.
23. Eltze E. Bettendorf O, Rody A. Jackisch C, Herchenroder F. Bocker W. Pfleiderer B (2003) Influence of local complications on capsule formation around model implants in a rat model. J Biomed Mater Res 64A:12-19.
24. Minami E. Jun Koh I, Ronche J C, Ferreira J. Logullo A F, Waitzberg A. Chifferi V, Fortoul-Rosewick T, Dominguez-Pereira M. Nascimento P H, Saldiva P. Poli de Figueiredo L F (2006) The composition and behavior of capsules around smooth and textured breast implants in pigs. Plast Reconstr Surg 118:874-884.
25. Eltze E, Schafer U, Bettendorf O, Rody A. Herchenroder F. Chiwritsch T, Jackisch C. Pfleiderer B (2006) Radiation-induced capsule tissue reactions around textured breast implants in a rat model. Breast 15:331-338.
26. Adams W P, Haydon M S. Raniere J, Trott S, Marques M. Feliciano M, Robinson J B. Tang L. Brown S A (2006) A rabbit model for capsular contracture: development and clinical implications. Plast Reconstr Surg 117:1214-1219.
27. Cardenas-Camarena L, Paillet J C, Briseno R: Electrostimulation (2005) Uses and applications for periprosthetic capsular contracture: Experimental model. Aesth Plast Surg 29:410-414.
28. Peterson H D. Burt G B Jr (1974) The role of steroid in prevention of circumferential capsular scarring in augmentation mammaplasty. Plast Reconstr Surg 54:28
29. Perrin E R (1976) The use of soluble steroid within inflatable breast prostheses. Plast Reconstr Surg 57:163
30. Vinnik C A (1976) Spherical contracture of fibrous capsules around breast implants: Prevention and treatment. Plast Reconstr Surg 58:555.

31. Ellemberg A H (1977) Marked thinning of the breast skin flaps after the insertion of implants containing triamcinolone. Plast Reconstr Surg 60:755.
32. Carrico T J, Cohen I K (1979) Capsular contracture and steroid related complication after augmentation mammoplasty: A preliminary study. Plast Reconstr Surg 64:377.
33. Baker J L Jr (1981) The effectiveness of alpha-tocopherol (vitamin E) in reducing the incidence of spherical contracture around breast implants. Plast Reconstr Surg 68:696.
34. Cucin R L, Guthrie R H, Graham M (1982) Rate of diffusion of Solu-Medrol across the silastic membranes of breast prostheses: An in vivo study. Ann Plast Surg 9:228.
35. Cafee H H (1984) The effects of intraprosthetic methylprednisolone on implants capsules and surrounding soft tissue. Ann Plast Surg 12:348.
36. Gayou R. Rudolph R (1979) Capsular contraction around silicone mammary prostheses. Ann Plast Surg 2:62.

The invention claimed is:

1. A method for treating liver cirrhosis comprising administering to a subject in need thereof, a composition in sustained-release tablet form comprising 100 mg to 2400 mg pirfenidone, microcrystalline cellulose, low viscosity hydroxypropylmethylcellulose (HPMC), high viscosity hydroxypropylmethylcellulose (HPMC), silicon dioxide, and sodium stearyl fumarate.

2. A method for treating liver cirrhosis comprising administering to a subject in need thereof, a composition in sustained-release tablet form comprising 100 mg to 2400 mg pirfenidone, wherein the sustained-release tablet has a bioavailability of up to 12 hours.

3. The method of claim 2, wherein the composition comprises 600 mg of pirfenidone.

4. The method of claim 2, wherein the composition comprises 400 mg of pirfenidone.

5. The method of claim 2, wherein the composition comprises 600 mg to 2400 mg of pirfenidone.

6. The method of claim 1, wherein the sustained-release tablet has a bioavailability of up to 12 hours.

7. The method of claim 2, wherein the composition comprises 118.8 mg microcrystalline cellulose, 70.0 mg low viscosity hydroxypropylmethylcellulose (HPMC), 46.5 mg high viscosity hydroxypropylmethylcellulose (HPMC), 8.5 mg silicon dioxide, and 6.2 mg sodium stearyl fumarate.

8. The method of claim 2, wherein the composition is administered for up to 6 months.

9. The method of claim 2, wherein the composition is administered for up to 12 months.

10. The method of claim 2, wherein the composition is administered for at least 12 months.

11. The method of claim 2, wherein the composition is administered orally at least one time per day.

12. The method of claim 2, wherein the composition is administered orally 2 times per day.

13. The method of claim 2, wherein the composition is administered orally 3 times per day.

14. The method of claim 2, wherein the composition is administered orally 1 to 4 times per day.

15. The method of claim 2, wherein a daily dosage comprises 400 mg to 2400 mg of pirfenidone per day.

16. The method of claim 2, wherein a daily dosage comprises up to 2400 mg of pirfenidone per day.

17. The method of claim 2, wherein a daily dosage comprises up to 1400 mg per $m^2$ body surface area (BSA) of pirfenidone per day.

18. A method for treating liver fibrosis comprising administering to a subject in need thereof, a composition in sustained-release tablet form comprising 100 mg to 2400 mg pirfenidone, microcrystalline cellulose, low viscosity hydroxypropylmethylcellulose (HPMC), high viscosity hydroxypropylmethylcellulose (HPMC), silicon dioxide, and sodium stearyl fumarate.

19. The method of claim 18, wherein the composition comprises 600 mg of pirfenidone.

20. The method of claim 18, wherein the composition is administered orally 2 times per day.

* * * * *